(12) United States Patent
Hill et al.

(10) Patent No.: US 7,338,204 B2
(45) Date of Patent: Mar. 4, 2008

(54) MEASUREMENT APPARATUS AND METHOD

(75) Inventors: Harold Keith Hill, Hamilton (NZ); Simon James Lovatt, Hamilton (NZ); Philip Edward Petch, Hamilton (NZ)

(73) Assignee: AgResearch Limited, Hamilton (NZ)

( * ) Notice: Subject to any disclaimer, the term of this patent is extended or adjusted under 35 U.S.C. 154(b) by 90 days.

(21) Appl. No.: 10/539,867

(22) PCT Filed: Dec. 17, 2003

(86) PCT No.: PCT/NZ03/00279

§ 371 (c)(1),
(2), (4) Date: Jan. 13, 2006

(87) PCT Pub. No.: WO2004/055504

PCT Pub. Date: Jul. 1, 2004

(65) Prior Publication Data

US 2006/0153271 A1    Jul. 13, 2006

(30) Foreign Application Priority Data

Dec. 17, 2002 (NZ) ..................... 522635

(51) Int. Cl.
*G01J 5/00* (2006.01)
(52) U.S. Cl. .................... 374/121; 374/141
(58) Field of Classification Search ........... 374/121, 374/141
See application file for complete search history.

(56) References Cited

U.S. PATENT DOCUMENTS

| 4,767,981 A | * | 8/1988 | Pakulis ................ 324/640 |
| 4,870,234 A | | 9/1989 | Steers et al. |
| 5,341,814 A | | 8/1994 | Van De Velde et al. |
| 6,132,084 A | | 10/2000 | Whipple, III et al. |
| 6,849,852 B2 | * | 2/2005 | Williamson .......... 250/341.6 |
| 2003/0024315 A1 | * | 2/2003 | Merkel et al. ............ 73/596 |
| 2003/0072409 A1 | * | 4/2003 | Kaufhold et al. ........... 378/53 |

FOREIGN PATENT DOCUMENTS

| EP | 1 224 905 A2 | 7/2002 |
| FR | 2 705 441 A1 | 11/1994 |
| JP | 04-008634 | 8/1993 |
| WO | WO 92/14164 | 8/1992 |
| WO | WO 01/67057 A1 | 9/2001 |
| WO | WO 02/48665 A1 | 6/2002 |

\* cited by examiner

*Primary Examiner*—Gail Verbitsky
*Assistant Examiner*—Megann E Vaughn
(74) *Attorney, Agent, or Firm*—Blakely, Sokoloff, Taylor & Zafman; Stephen M. De Klerk

(57) ABSTRACT

An apparatus (1) for measuring the transmission or attenuation of electromagnetic radiation through an object (6), said apparatus including an electromagnetic radiation emitter (2) and detector (3), characterised in that to perform transmission/attenuation measurements, the apparatus in configurable such that said emitter (2) is positioned immediately adjacent the surface of said object (6) and said detector (3) is positioned on an opposing side of the object (6) such that the detector (3) solely, or at least substantially receives electromagnetic radiation transmitted through the object (6) from the emitter (2).

15 Claims, 4 Drawing Sheets

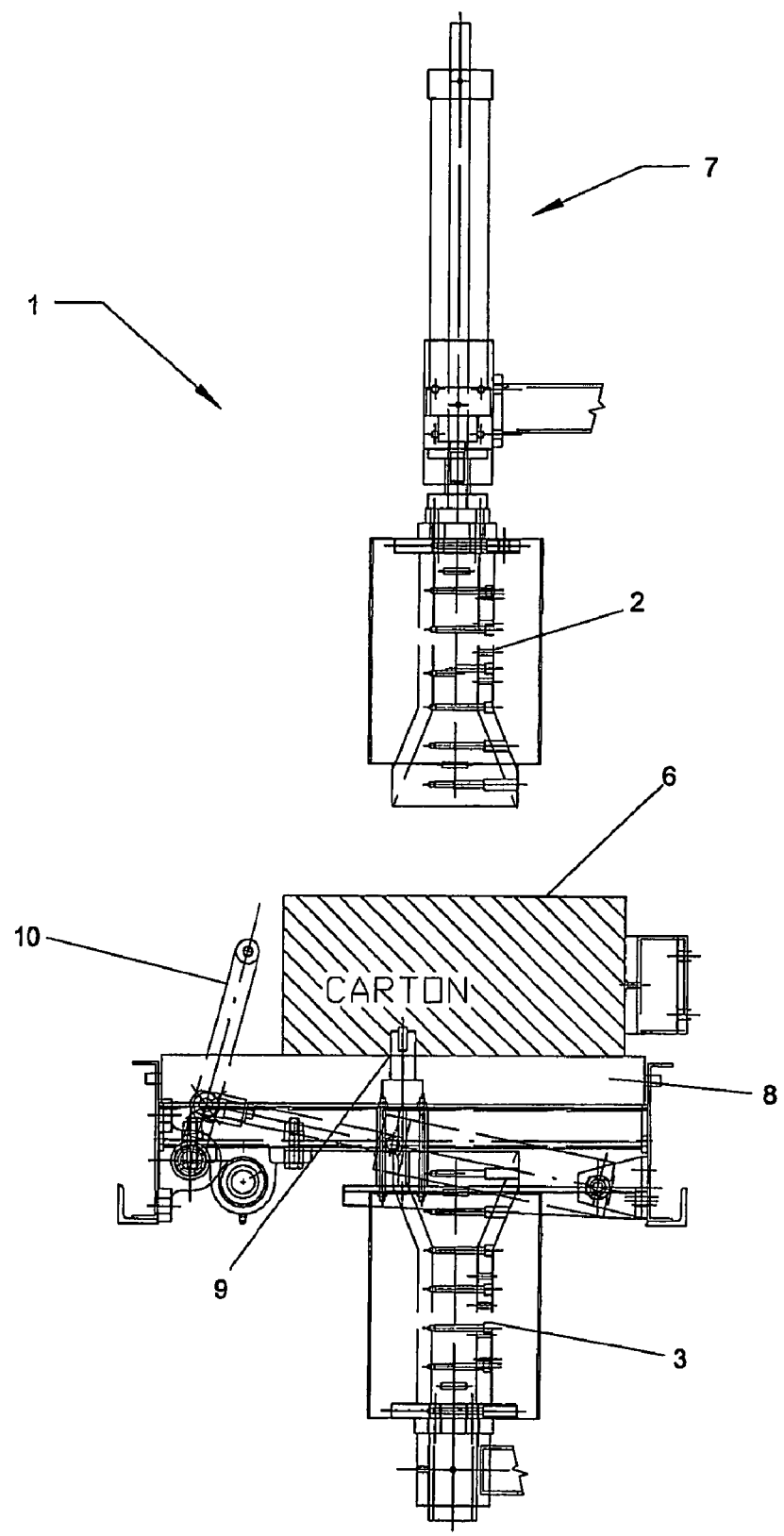

MEASUREMENT APPARATUS AND METHOD

CROSS-REFERENCE TO OTHER APPLICATIONS

This is a National Phase of International Application No. PCT/NZ2003/000279, filed on Dec. 17, 2003, which claims priority from New Zealand Patent Application No. 522635, filed on Dec. 17, 2002.

TECHNICAL FIELD

The present invention relates to a means of measuring the transmission of electromagnetic radiation through a sample, and more particularly to a means for temperature measurement of frozen/chilled organic matter such as frozen meat.

BACKGROUND ART

The practice of chilling and freezing produce for both transport and storage has gained widespread acceptance and is the primary method of ensuring food preservation in the journey from the food processing plant to the customer. Bacterial growth poses a serious health risk for food which is not maintained at a safe temperature during the different stages in the supply chain, typically including the end of production line packaging, storage on the manufacturers' premises, transit, and arrival at the retailer.

As a visual inspection of frozen food is incapable of determining the core temperature, the current standard procedure to determine whether a product is correctly frozen requires insertion of a thermometer/thermal sensor through a hole drilled into the produce, and typically also through the product container. Such a procedure is time consuming, difficult to automate and detrimental to the product tested. Furthermore, as frozen food products are often transported between several locations and storage sites such as in the export of frozen meat from a remote country such as New Zealand, this invasive temperature testing procedure would need to be repeated on numerous occasions.

It is thus unsurprising that such invasive temperature testing procedures are sometimes omitted in practice with the resultant risks that foodstuffs may be either insufficiently frozen (with the corresponding health dangers) or alternatively that time and energy is wasted due to excessive freezing.

In order to address these difficulties, significant research has been devoted to non-invasive methods of temperature sensing. Microwave radiation interacts with organic matter in a manner which is particularly effective in relation to temperature measurement of frozen or chilled food.

Microwaves are a form of energetic electromagnetic radiation capable of penetrating matter to a degree dependant on the radiation energy and the matter composition. Although the strict numerical definition is subject to change by the Industrial, Scientific and Medical (ISM) standards, microwaves are currently recognised generally as radiation having a frequency of approximately 100 MHz-300 GHz. Microwave radiation is used as a heating medium due to its capacity for stimulation or vibration of water molecules in organic matter thus causing localised temperature increases.

However, the interaction of microwaves with organic matter is also temperature dependant. Microwave radiation is attenuated by passage through a given material according to a function which includes dependencies on both the temperature of the material and the frequency of the incident microwave radiation.

Significantly, the attenuation of the microwave radiation by the sample material drops sharply for temperatures below the freezing point, i.e., the material effectively becomes transparent to microwave radiation. This characteristic change in attenuation is a well-known feature of the interaction of microwaves and frozen produce.

Whilst this sharp change in transmittance (i.e. the inverse of attenuation) above and below the borderline of freezing temperatures may be used to indicate when a product is definitely frozen, determining the exact temperature of a lightly frozen or chilled item requires an accurate measurement system with an elimination of unknown variables and other error sources. It is known to use a sensor or detector to measure the un-attenuated microwave radiation passing through the sample as a fraction of the total microwave radiation transmitted by the microwave transmitter. This result may be used as a basis for calculating the temperature, or 'ice-fraction' of the sample.

However, the accuracy of such a system may be undermined by a number of factors. The microwave detector will be unable to discriminate between a microwave ray detected after transmission through the sample body and a ray which has been reflected from some other object, or even received directly from the transmitter without having been transmitted through or reflected from anything, including the sample. Without eliminating or otherwise accounting for such potential error sources such as alternate beam paths, the detector will receive a false reading, resulting in incorrectly calculated sample temperature.

Various solutions to this difficulty have been attempted.

Miyakawa, M. (1993) *Tomographic measurement of temperature change in phantoms of the human body by chirp radar-type microwave computed tomography*, [Med. & Biol. Eng. & Comput., 31, S31-S36.] developed a microwave-based computed tomography system to measure temperature in the human body. A pair of small (9.53 by 19.1 mm) antennae are rotated around a (phantom of a) body immersed in saline solution to measure the attenuation of the microwave signal at each step of the rotation. The individual measurements are then mathematically combined using a computer to generate an image of the microwave attenuation formed from two-dimensional slices through the body.

To eliminate the problem of alternate beam paths (i.e. paths not passing through the body) interfering with the measurement, Mikakawa (1993) uses a bath of saline. As saline has similar microwave attenuation to body fluid, immersing the body in saline minimises reflection and refraction as the beam enters the body. The body is then imaged at two different temperatures and the attenuations in the two images subtracted to show that they are different at different temperatures.

This technique has the drawbacks of;
the physical and practical inconvenience of using a saline bath to minimise reflection and refraction;
the requirement for a reference image to permit the subtraction of images to give a temperature measurement, and
a measurement time of at least several seconds.

U.S. Pat. No. 5,341,814 Van De Velde et al (1994) teaches of a method for measuring the temperature of an object by detecting the thermal noise emitted by the object in the microwave frequency range. However, Van De Velde does acknowledge the following difficulty;

In this connection, there are known microwave radiometry devices in which the microwave radiation emitted via an antenna is picked up and the signals received are routed to signal processing means which enable the temperature of the object in question to be determined.

However, one of the main problems encountered in microwave frequency radiometry resides in the matching of the antenna in respect of the material the temperature of which one wishes to know. Indeed, the antenna used has a reflection coefficient $R_o$ and, as a result, the antenna is never perfectly matched, given that the objects to be measured generally have different configurations, sizes and properties.

U.S. Pat. No. 4,346,716 Carr (1980) relates to the detection of tumours by measuring the differential rate at which tumours are heated by microwave energy compared with normal tissue, due to the fact that tumours are not cooled as effectively as normal tissue by flowing blood. The temperature measurement mechanism is based on passive measurements of microwave emissions at 4.7 GHz, (as per Van De Velde et al), rather than the transmittance measurement.

U.S. Pat. No. 4,870,234 Steers et al (1989) relies on the same fundamental mechanism discussed earlier to distinguish frozen from unfrozen product, i.e. a measurement of the different microwave transmittance through material dependent on whether it is frozen or unfrozen.

The Steers et al approach uses the rate of change in temperature of a reference material to measure the amount of microwave energy passing through the product rather than a microwave receiver. This method has the advantage of low cost and may provide an appropriate alternative in some applications. However, for applications requiring temperature measurement of products in systems with a high throughput rate (such as in a meat processing plant), the method of Steers et al suffers from three serious disadvantages:

1. a single temperature measurement requires sufficient time for the reference material to heat measurably—requiring seconds or even tens of seconds and thus limiting throughput;
2. the use of a microwave transmitter with sufficient power to measurably heat the reference material necessitates appropriate shielding structures which are generally inconvenient or impractical to implement in automated food processing plants, and there is no provision disclosed for cooling the reference sample to facilitate rapid repeat temperature measurements.
3. Irrespective of a possible resolution of the first two disadvantages listed above, the third disadvantage would still prevent practical temperature measurements in a multi-sample temperature measurement scenario. Due to the absence of any cooling, the reference sample would eventually be heated to an equilibrium temperature from repeated measurements, thus preventing further reference sample temperature change implicit for any sample temperature measurements.

The 'Celsius' unit by Loma Systems™ is a microwave temperature measurement device, resembling a domestic microwave oven. After a sample is manually placed inside the fully enclosed cabinet (via a front door), the sample is irradiated by microwave radiation and a temperature measurement is taken, though the specific measurement mechanism used is not disclosed by Loma Systems™ in their promotional literature.

However, from the configuration of the device, it seems likely a similar system to that of Van De Velde et al is utilised, i.e. the temperature is calculated from the microwave radiation emitted or reflected from the irradiated object.

If such a mechanism is employed, the detector also receives microwaves which have been deflected, reflected and refracted from the enclosure interior. The temperature measurement thus needs to take account of all the radiation detected and not just those microwaves emanating from the sample.

Whilst this system may be suitable for measuring samples small enough to fit in the enclosure, this system does not lend itself to multi-sample measurements in high throughput applications.

A housing completely enclosing each sample is an unavoidable requirement as the microwave measurements would otherwise be affected by stray environmental electromagnetic radiation. Such a requirement would necessitate complex and costly mechanical systems to repeatedly manipulate samples from a production line into a measurement housing, seal the enclosure, rapidly perform the temperature measurement, extract the sample and return to the production line.

It can be seen therefore that none of the above prior art provides a practical, non-invasive means suitable for incorporation in rapid sample throughput systems for determining the temperature of chilled or frozen produce or other water-rich substances.

Alternative forms of penetrative electromagnetic radiation may also be transmitted through a sample for a variety of reasons, e.g. to analyse the sample's constituents, or to measure the degree of transmission/attenuation of the sample to particular frequencies, to provide a heating effect, or the like. In such applications, it may be important to reduce measurement uncertainties caused by detecting radiation reflected via some circuitous route (e.g. from environmental conditions or structures) rather than was transmitted directly through the sample. Such non-microwave electromagnetic radiation (ranging from radio frequency waves to higher frequency radiation) may also suffer from the aforesaid disadvantages of microwave temperature measurement systems.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents.

It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided an apparatus for measuring the transmission or attenuation of electromagnetic radiation through an object, said apparatus including an electromagnetic radiation emitter and detector, characterised in that the apparatus further includes a drive apparatus capable of reversibly placing the said emitter immediately adjacent or in contact with a surface of the object such that any emitted electromagnetic radiation from the emitter is transmitted into the object, wherein to perform transmission/attenuation measurements, said emitter is positioned by said drive apparatus immediately adjacent or in contact with the surface of said object and said detector is positioned on an opposing side of the object such that the detector receives electromagnetic radiation transmitted through the object from the emitter The present invention thus provides a means of mitigating measurement errors stemming from any detector readings of indirectly received electromagnetic radiation not passing though the object. This is particularly useful for temperature measurements, where the transmissivity of the object to the incident electromagnetic radiation varies according to temperature.

Thus, according to one embodiment of the present invention, said apparatus is configurable to perform temperature measurements by positioning of the emitter immediately adjacent or in contact with the surface of said object and positioning said detector on an opposing side of the object such that the detector receives electromagnetic radiation transmitted through the object from the emitter.

In particular, the invention is suited to, but not restricted to, temperature measurements using microwave radiation.

According to one embodiment of the present invention there is provided an apparatus for measuring the temperature of an object, said apparatus including:

a microwave emitter and a microwave detector characterised in that the apparatus further includes a drive apparatus capable of reversibly placing the said emitter immediately adjacent to, or in contact with, a surface of the object, wherein to perform temperature measurements, said microwave emitter is positioned by said drive apparatus immediately adjacent the surface of said object and said detector is positioned on an opposing side of the object such that the microwave detector receives microwave radiation transmitted through the object from the microwave emitter.

According to another aspect of the present invention there is provided a method of measuring the temperature of an object using microwave radiation using the apparatus as described above, said method characterised by the steps of:

using said apparatus to position the microwave emitter immediately adjacent or in contact with a surface of said object;

positioning a microwave detector on an opposing side of the object to said emitter;

such that the microwave detector receives microwave radiation transmitted through the object from the microwave emitter.

As used herein, the term object is to be interpreted widely and includes any substance, material, or organic matter, particularly those containing moisture and/or any other substance where the transmittivity of electromagnetic radiation energy changes measurably with temperature.

In one embodiment, said object is frozen, near frozen or chilled.

It will be appreciated however that the present invention is not necessarily limited to the temperature measurements of frozen or chilled objects. Alternative (non-temperature related) uses may be made of the measurements produced by the present invention.

Optionally, the present invention also includes drive apparatus capable of reversibly placing the detector on an opposing side of said object to said emitter.

According to one aspect of the present invention, said drive apparatus is a linear actuator including, but not limited to, pneumatic, hydraulic, electro-mechanical operated actuators.

The drive apparatus/emitter assembly may further include a proximity sensor capable of determining the proximity of the object to the emitter. Thus, the emitter may be reliably and repeatably placed at the same degree of proximity to each object without risk of impact. In one embodiment, the proximity sensor is an ultrasonic sensor.

Preferably, said detector is positioned immediately adjacent to or in contact with said object. However, in an alterative embodiment, said detector is located proximate to, but not in contact with said object.

The present invention as described above confers a number of advantages over the prior art. There is no restriction on the object size due to the need to place the object in an enclosure. Furthermore, the possible detection of erroneous electromagnetic radiation not transmitted through the object is practically eliminated by placing the transmitter adjacent the object surface. Placing the detector (as well as the emitter) immediately adjacent or in contact with the object also aids in ensuring only microwaves transmitted through the object (or at least substantially only these microwaves) are detected. Surprisingly, it has been found that locating the detector at a short distance from the object does not necessarily corrupt accurate measurements.

The present invention is also ideally suited to rapid repeat temperature measurements of objects on a production line or the like. As there is no requirement for placing the object in a housing or enclosure, the dwell-time between measurements is not exacerbated by removing the objects from a conveyor system or the like, placing in an enclosure for measurement, and (possibly) replacing on the conveyor system. Instead, the temperature of chilled or frozen objects may be measured directly on a conveyor or similar, thus speeding throughput significantly.

Thus, according to a further embodiment, said object is placed on a moving conveyance located between the emitter and detector.

A moving conveyance includes, but is not limited to, conveyor systems, pallet handling systems, automated cargo transport systems, robotic, manual or other human operated object handling and transportation systems and the like.

Preferably, said conveyance has a primary axis of travel.

According to one aspect of the present invention, said drive apparatus is a linear actuator operating substantially orthogonally to said primary axis of the conveyance.

In embodiments using objects of highly uniform size and positioning on the conveyance means, it may be possible for the conveyance means to transport the object immediately adjacent to the emitter without the need to move the emitter, i.e., eliminating the need for an actuator.

Thus, temperature measurements of successive objects may be provided by the combined operation of said conveyance system moving successive objects along said primary axis of travel between the emitter and detector and a said linear actuator moving the emitter (and optionally) the detector into and out of contact with an object when interposed between said emitter and detector.

It is thus also possible to scan a large object by making repeated temperature measurements at different points or even continuous measurements as the emitter/detector is moved over the surface of the object.

However, it will be appreciated that the present invention need not necessarily be used in automated or multi object measurement application. The advantages of both simplified equipment over other electronic non-invasive systems together with the improved accuracy, convenience and non-invasive characteristics compared to drilled core samples favour the present invention for any scale of operation/application.

It is entirely feasible for an operator to manually place the emitter and detector on opposing sides of an object for a singular temperature measurement.

According to a further aspect, the present invention provides a method of measuring the transmission or attenuation of electromagnetic radiation through successive objects using the apparatus as hereinbefore described, comprising the steps;
  successively transporting objects via said conveyance system between the emitter and detector along the primary axis of travel;
  positioning the emitter adjacent to, or in contact with, each object when interposed between said emitter and detector;
  performing an electromagnetic radiation transmission or attenuation measurement;
  moving the emitter away from the object.

Preferably, the method further includes the steps of:
  positioning the detector adjacent to, or in contact with, each object when interposed between said emitter and detector prior to performing the electromagnetic radiation transmission or attenuation measurement;
  moving the detector away from the object.

According to one aspect, the apparatus is located and operable external to any enclosure or housing.

According to a further preferred embodiment, the present invention provides a method of measuring temperature of an object using microwave radiation using the apparatus substantially as described herein, said method characterised by the steps of:
  using said drive apparatus to position the microwave emitter immediately adjacent or in contact with a surface of said object;
  irradiating the object with microwave radiation from the emitter;
  detecting microwave radiation transmitted through the object with the microwave detector positioned on an opposing side of the object to said emitter
  calculating the object temperature from said microwave radiation received by the detector.

As previously stated, the inventive emitter and detector configuration may also be utilised with other forms of electromagnetic radiation and for non-temperature measurement purposes.

BRIEF DESCRIPTION OF DRAWINGS

Further aspects of the present invention will become apparent from the following description which is given by way of example only and with reference to the accompanying drawings in which:
FIG. 4 shows an enlarged view of the embodiment shown in FIG. 2.

BEST MODES FOR CARRYING OUT THE INVENTION

FIGS. 1-4 show a first embodiment of the present invention for temperature measurement of frozen meat boxes in a meat processing plant.

Figure 1:
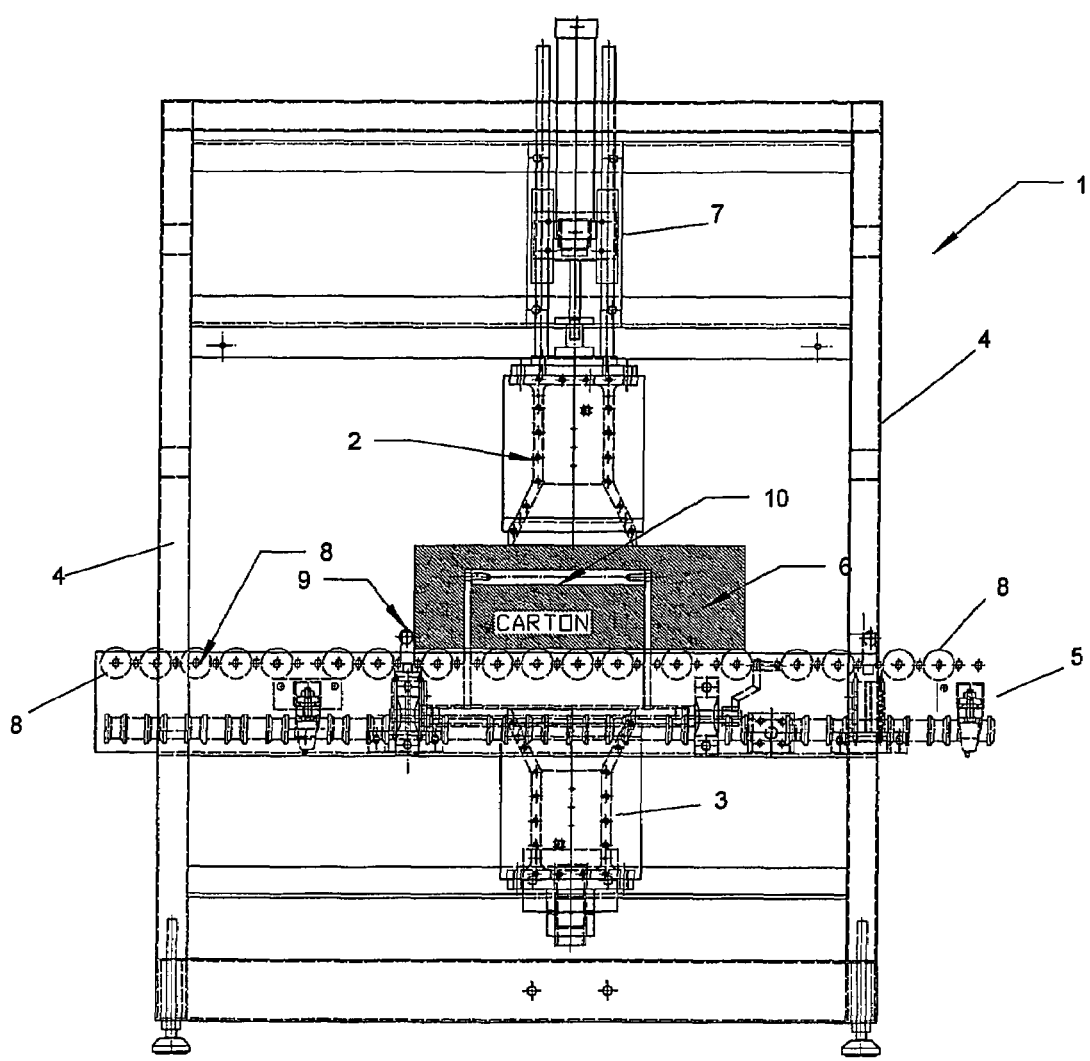
FIG. 1 shows a first side elevation of a preferred embodiment of the present invention.
Figure 2:
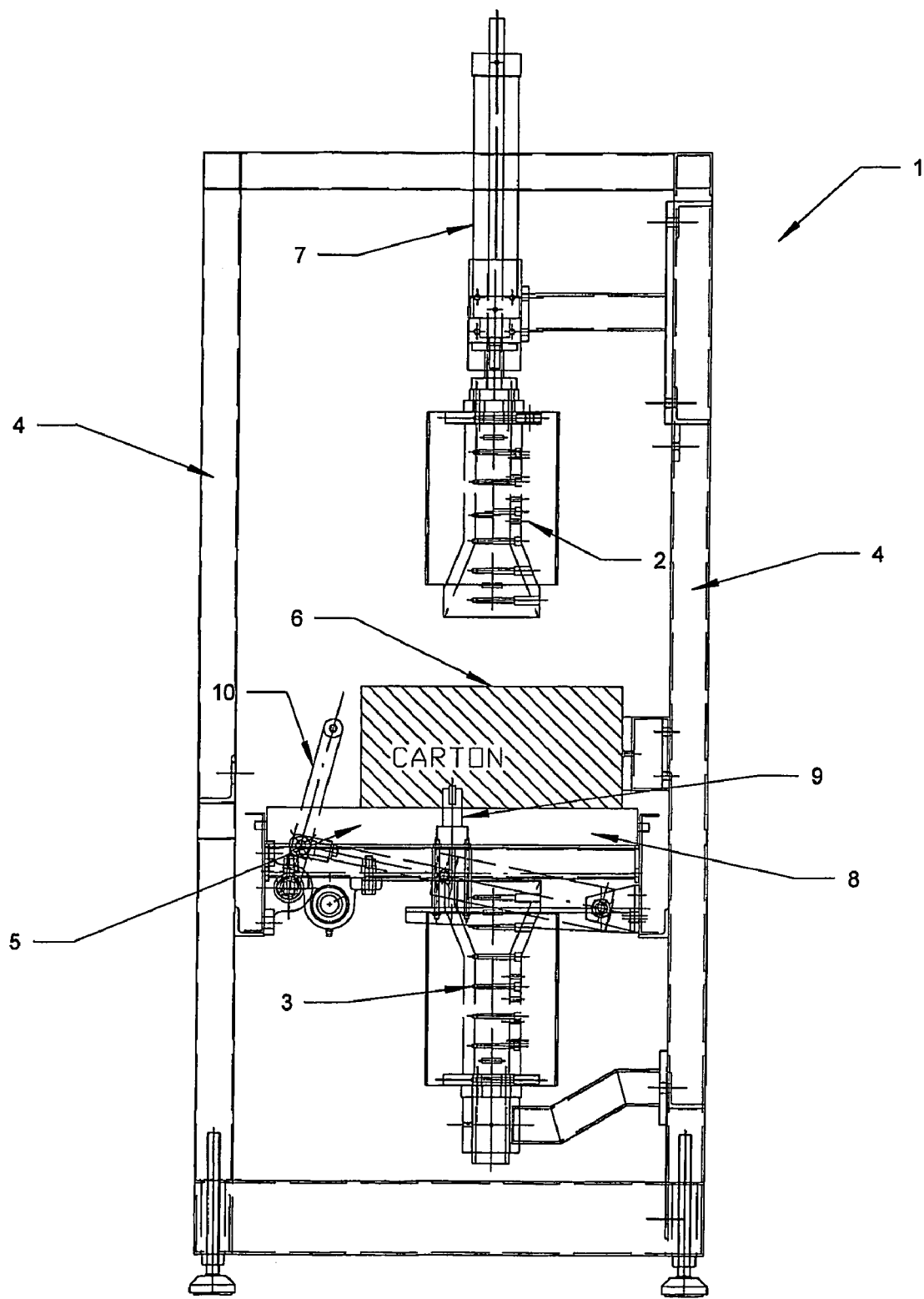
FIG. 2 shows a second side elevation of the embodiment shown in FIG. 1.

FIGS. 1 and 2 show an embodiment of the present invention in the form of a microwave temperature measurement apparatus (1), comprised of a microwave emitter (2), a microwave detector (3), support frame (4) and a moving conveyance system in the form of conveyor system (5). This embodiment is primarily configured for measuring the temperature of frozen meat placed in standard meat cartons (6). However, the temperature measurement of alterative organic produce such as cheese, fish or poultry may also be performed. Testing by the applicant has determined the successful functioning of the present invention with each such produce.

Furthermore, the use of microwave radiation is exemplary and is not limiting. Alternative forms of electromagnetic radiation may be employed according to the specific requirements of the application without departing from the inventive configuration of the emitter and detector described herein.

Figure 3:
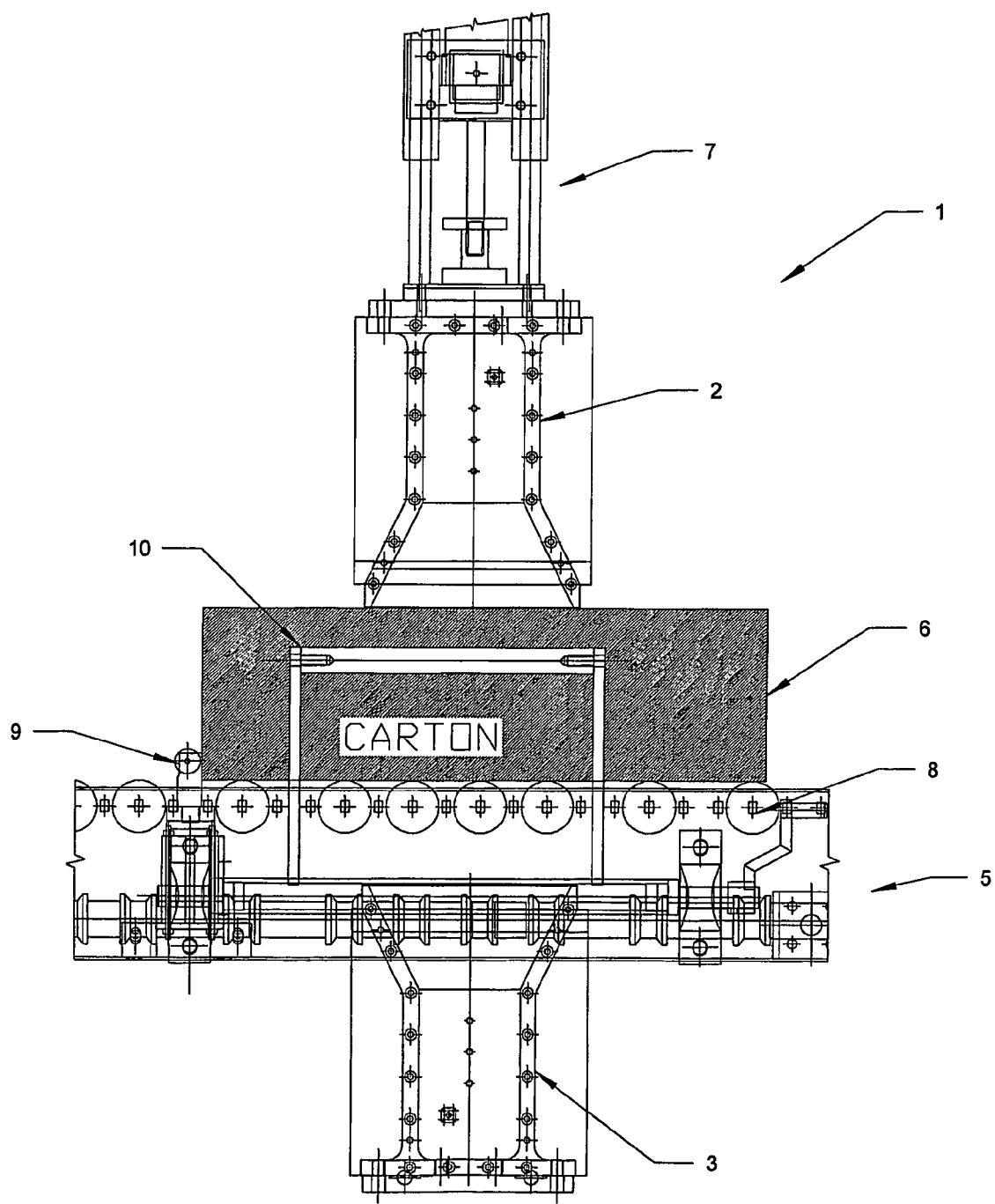
FIG. 3 shows an enlarged view of the embodiment shown in FIG. 1.

FIGS. 3 and 4 show enlarged representations of the microwave emitter and detector (2, 3), conveyor assembly (5) and carton (6). The microwave emitter (2) is located at the lower end of a drive apparatus in the form of a vertically orientated linear actuator (7) whilst the microwave detector (3) is fixed below the conveyor system (5) in a confronting relationship directly below the microwave emitter/actuator assembly (2, 7).

The microwave detector (3) and the exterior housing of the actuator (7) are secured to the support frame (4). The conveyor system (5) is formed from a plurality of cylindrical rollers (8) located transversely across the width of the conveyor (5). Meat cartons (6) are driven along the conveyor (5) either actively or under the influence of gravity by inclining the conveyor (5).

The primary axis of travel of the cartons (6) along the conveyor (5) passes between the microwave emitter and detector (2, 3) at which point a stop cylinder (9) raises from below the plane of the conveyor (5) surface to restrain the carton (6) while a temperature measurement is taken. A nudge bar (10) positions each carton laterally to align with the emitter/detector (2, 3) to account for any variation in alignment as cartons are transported on the conveyor (5).

When the carton (6) is correctly positioned by the stop cylinder (9) and nudge bar (10) between the microwave emitter and detector (2, 3) respectively, the linear actuator (7) lowers the emitter (2) to a position immediately adjacent the surface of the carton (6). The position of the emitter (2) with respect to the carton (6) is governed by an ultrasonic proximity sensor (not shown). Thus, the emitter (2) may be rapidly and repeatably placed in the same proximity to each successive carton (6) without risk of impact or the need for manual intervention. Alternative proximity, contact or position sensors may be utilized instead of an ultrasonic sensor.

The microwave emitter (2) is then activated and a pulse of microwaves (not shown) is transmitted through the carton (6) towards the detector (3). The degree of attenuation of the transmitted microwave beam provides an indication of the temperature of the carton (6) and its contents, i.e. the frozen meat.

As the emitter is placed directly on the surface of the carton, virtually all the microwaves emitted have to travel through the carton (6) before being either absorbed, or detected by the detector (3). This configuration reduces the possibility for any external reflection, refraction or other indirect routes from the emitter (2) to the detector (3).

Although the above embodiment shows the use of temperature measurements with a standard sized meat container, it will be appreciated that a variety of other objects/containers may be employed by configuring and dimensioning the present invention (1) accordingly. It will be further appreciated that alternative conveyance means to the conveyor system (5) may be employed.

In the embodiment shown, the microwave detector (3) is positioned a short distance below the carton (6) to allow for the passage of the conveyor system (5). It will be appreciated that in other embodiments, the detector (3) may be placed in contact with or immediately adjacent to the surface of the carton (6) to ensure no extraneous reflected or refracted microwaves are received by the detector (3). It has been found in practice however that separating the detector (3) from the surface of the object being the temperatures being measured (6) does not cause any appreciable degradation in the temperature measurement. Nevertheless, alternative detector/conveyor systems (3, 5) may be configured to permit placement of the detector (3) in contact with, or immediately adjacent to, the carton (6).

In yet further embodiments, the emitter (2) and detector (3) may be manually placed in position about the carton (6) to effect a single temperature measurement, as may be required for random sampling checks and the like.

Thus, by virtue of the aforementioned configuration, the present invention provides an apparatus and a method for measuring the transmission/attenuation of electromagnetic radiation transmitted through a sample without erroneous measurements from non-transmission radiation and without need to place the said objects in a measurement enclosure and without obstructing the throughput of object in continuous production/packaging or storage applications.

Aspects of the present invention have been described by way of example only and it should be appreciated that modifications and additions may be made thereto without departing from the scope thereof.

The invention claimed is:

1. An apparatus for measuring the transmission or attenuation of electromagnetic radiation through an object, said apparatus including an electromagnetic radiation emitter and detector, characterised in that the apparatus further includes a drive apparatus capable of reversibly placing the said emitter immediately adjacent or in contact with a surface of the object such that any emitted electromagnetic radiation from the emitter is transmitted into the object, and a proximity sensor capable of determining the proximity of the object to the emitter, wherein to perform transmission/attenuation measurements, said emitter is positioned by said drive apparatus immediately adjacent or in contact with the surface of said object and said detector is positioned on an opposing side of the object such that the detector receives electromagnetic radiation transmitted through the object from the emitter.

2. The apparatus as claimed in claim 1, wherein said apparatus is configurable to perform temperature measurements by positioning of the emitter immediately adjacent or in contact with the surface of said object and positioning said detector on an opposing side of the object such that the detector receives any electromagnetic radiation transmitted through the object from the emitter.

3. The apparatus as claimed in claim 1, wherein said object includes any substance, material, or organic matter containing moisture and/or any other substance where the transmittivity of electromagnetic radiation energy changes measurably with temperature.

4. The apparatus as claimed in claim 1, wherein said object is frozen, near frozen or chilled.

5. The apparatus as claimed in claim 1, wherein said drive apparatus is capable of reversibly placing the said microwave detector on an opposing side of said object to said emitter.

6. The apparatus as claimed in claim 1, wherein said drive apparatus is a pneumatic, hydraulic, or electro-mechanical operated linear actuator.

7. The apparatus as claimed in claim 1, wherein the proximity sensor is an ultrasonic sensor.

8. The apparatus as claimed in claim 1, wherein said detector is positionable immediately adjacent to, or in contact with, said object.

9. The apparatus as claimed in claim 1, wherein said detector is located proximate to, but not in contact with said object.

10. The apparatus as claimed in claim 1, further including a moving conveyance configured to transport a plurality of objects along a primary axis of travel passing between the emitter and detector.

11. The apparatus as claimed in claim 10, wherein the moving conveyance includes conveyor systems, pallet-handling systems, automated cargo transport systems, robotic, manual or human-operated object handling and/or transportation systems.

12. A method of measuring the transmission or attenuation of electromagnetic radiation through successive objects using the apparatus claimed in claim 10, comprising the steps:
   successively transporting objects via said conveyance system between the emitter and detector along the primary axis of travel;
   positioning the emitter adjacent to, or in contact with, each object when interposed between said emitter and detector;
   performing an electromagnetic radiation transmission or attenuation measurement; and
   moving the emitter away from the object.

13. The method as claimed in claim 12 including the further steps of:
   positioning the detector adjacent to, or in contact with, each object when interposed between said emitter and detector prior to performing the electromagnetic radiation transmission or attenuation measurement; and
   moving the detector away from the object.

14. The method as claimed in claim 12, wherein the apparatus is located and operable external to any enclosure or housing.

15. A method of measuring temperature of an object using microwave radiation using the apparatus as claimed in claim 1, said method characterised by the steps of:
   using said drive apparatus to position the microwave emitter immediately adjacent or in contact with a surface of said object;
   irradiating the object with microwave radiation from the emitter;
   detecting microwave radiation transmitted through the object with the microwave detector positioned on an opposing side of the object to said emitter; and
   calculating the object temperature from said microwave radiation received by the detector.

* * * * *